(12) United States Patent
Bloemer

(10) Patent No.: US 8,692,843 B2
(45) Date of Patent: Apr. 8, 2014

(54) METHOD FOR GRAPHICAL DISPLAY AND MANIPULATION OF PROGRAM PARAMETERS ON A CLINICAL PROGRAMMER FOR IMPLANTED DEVICES AND CLINICAL PROGRAMMER APPARATUS

(75) Inventor: Frank Bloemer, Berlin (DE)

(73) Assignee: Biotronik SE & Co. KG, Berlin (DE)

( * ) Notice: Subject to any disclaimer, the term of this patent is extended or adjusted under 35 U.S.C. 154(b) by 183 days.

(21) Appl. No.: 13/370,311

(22) Filed: Feb. 10, 2012

(65) Prior Publication Data

US 2012/0229496 A1  Sep. 13, 2012

Related U.S. Application Data

(60) Provisional application No. 61/451,129, filed on Mar. 10, 2011.

(51) Int. Cl.
*G09G 5/02* (2006.01)
*A61N 1/08* (2006.01)
*G09G 5/06* (2006.01)

(52) U.S. Cl.
CPC ....................................... *G09G 5/06* (2013.01)
USPC ............................................ 345/593; 607/62

(58) Field of Classification Search
CPC ....................................... G09G 5/06
USPC ........................................................... 345/593
See application file for complete search history.

(56) References Cited

U.S. PATENT DOCUMENTS

| | | | | |
|---|---|---|---|---|
| 6,166,710 | A * | 12/2000 | Havel ............................... | 345/46 |
| 6,985,141 | B2 * | 1/2006 | Abe et al. ....................... | 345/204 |
| 7,352,368 | B2 * | 4/2008 | Frazelle et al. ................ | 345/419 |
| 8,351,480 | B2 * | 1/2013 | Allie ................................ | 372/55 |
| 2005/0110791 | A1 * | 5/2005 | Krishnamoorthy et al. .. | 345/419 |
| 2011/0172744 | A1 * | 7/2011 | Davis et al. ..................... | 607/62 |

* cited by examiner

*Primary Examiner* — David T Welch
*Assistant Examiner* — Yuehan Wang
(74) *Attorney, Agent, or Firm* — ARC IP Law, PC; Joseph J. Mayo

(57) ABSTRACT

Accepts inputs via an input device and displays resulting power consumption for example in a color-coded format that enables a doctor or other programmer to observe how changes in one programming parameter affects power consumption. This enables the apparatus to accept input values and display the resulting power consumption that would occur if the input values were programmed into an implantable device in an intuitive graphical manner. In one or more embodiments programming parameters associated with power consumption may be set for electrical stimulation pulses, namely the voltage amplitude, the frequency of pulses per unit time and the pulse width of the pulses in units of time.

16 Claims, 7 Drawing Sheets

METHOD FOR GRAPHICAL DISPLAY AND MANIPULATION OF PROGRAM PARAMETERS ON A CLINICAL PROGRAMMER FOR IMPLANTED DEVICES AND CLINICAL PROGRAMMER APPARATUS

This application claims the benefit of U.S. Provisional Patent Application 61/451,129 filed on 10 Mar. 2011, the specification of which is hereby incorporated herein by reference.

BACKGROUND OF THE INVENTION

1. Field of the Invention

At least one embodiment of the invention relates to a programming interface and associated clinical programmer used to program an implantable device. More particularly, but not by way of limitation, one or more embodiments of the invention enable a method for graphical display and manipulation of program parameters on a clinical programmer for implanted devices and clinical programmer apparatus.

2. Description of the Related Art

Neuro IPGs (Implanted Pulse Generators) for neurostimulation for SCS (Spinal Cord Stimulation) and DBS (Deep Brain Stimulation) and PNS (Periferal Nerve Stimulation) electrically stimulate a patient with electrical pulses. The pulses are generated by neuro IPG's according to programs. Programs control the timing and strength of the pulses according to program parameters such as:

Frequency
Amplitude (voltage or current)
Pulse width

Programming an IPG may be performed through use of programmers such as, but not limited to computers, hand held computers, tablet computers, patient or doctor devices or any other type of programmers that are configured to communicate a program to an IPG.

Based on the parameters utilized by the program, for example frequency, amplitude and pulse width, and in addition lead impedance, different power consumption occurs. Different power consumption yields different recharge-intervals (system with secondary, rechargeable cells) or expected service time (system with primary cells, non-rechargeable). Unfortunately, known programmers do not provide visually intuitive displays in which to determine how the setting of various parameters affects power consumption and recharge-intervals.

Therefore, it would be beneficial if the programming of IPGs included measures to manipulate these parameters in an intuitive manner that shows for example how the alteration of one or more parameters affects power consumption and recharge-intervals, which known devices to not allow. Thus there is a need for a method for graphical display and manipulation of program parameters on a clinical programmer for implanted devices and associated clinical programmer.

BRIEF SUMMARY OF THE INVENTION

One or more embodiments of the invention enable a method for graphical display and manipulation of program parameters on a clinical programmer for implanted devices and clinical programmer apparatus. Embodiments of the invention accept inputs via an input device and display resulting power consumption for example in a color-coded format that enables a doctor or other programmer to observe how changes in one programming parameter affects power consumption. This enables the apparatus to accept input values and display the resulting power consumption that would occur if the input values were programmed into an implantable device. In one or more embodiments programming parameters associated with power consumption may be set for electrical stimulation pulses, namely the voltage amplitude, the frequency of pulses per unit time and the pulse width of the pulses in units of time.

In one or more embodiments, the programming parameters include three parameters and hence, the apparatus will display the programming parameters using a triangle, further including a three sided shape, otherwise known as a surface herein as determined by the values of the parameters on the three axes.

If the settings of the programming parameters indicate moderate current consumption, the surface may be displayed in a certain colour (e.g. Yellow). If parameters are changed and increased current consumption is calculated, the colour of the triangle changes (for example to Red) If a program with a high current consumption is calculated, that colour changes for example to red, indicating, that this program will have high energy consumption or may not be programmed permanently.

Programming parameters can be changed by moving dots for example on each respective axis associated with a programming parameter for example via a touch screen display. Alternatively or in combination, programming parameters may be changed via sliding bars, or "sliders" or any other type of user interface input.

In other embodiments, energy consumption, or recharge intervals (which can be calculated with the resulting energy consumption) or remaining service time (which can be calculated with the resulting energy consumption and remaining battery capacity) can be automatically calculated and displayed on an additional axis. This resulting axis and the dot may or may be not manipulated by moving the dot on a touch screen, depending on the implemented features. For example, at least one embodiment enables accepting a touch screen input to move a dot associated with desired energy consumption or remaining service time, wherein the system automatically calculates the pulse width, amplitude and frequency to achieve the desired energy consumption or remaining service time for example, which is unknown in the art.

For embodiments that utilize more than three programming parameters (duty cycle, programmed on/off periods etc) the display may be output as a tetragon or pentagon or other respective polygon.

In a further embodiment the touch screen display provides tactile feedback after calculating the parameter configurations.

In a further embodiment the colours of the triangles is mixed from the RGB (red, yellow, blue) colours, depending on the different contributions of the different parameters (eg. Amplitude green, frequency yellow and pulse width red). Furthermore, any desired color or pattern may be utilized to represent any desired parameter in keeping with the spirit of the invention.

In a further embodiment the triangles or polygons from past parameter sets are displayed as a staple of the triangles or polygons, which can be easily searched in both directions, from the bottom or the top.

BRIEF DESCRIPTION OF THE DRAWINGS

The above and other aspects, features and advantages of the invention will be more apparent from the following more particular description thereof, presented in conjunction with the following drawings wherein.

DETAILED DESCRIPTION

A method for graphical display and manipulation of program parameters on a clinical programmer for implanted devices and associated clinical programmer will now be described. In the following exemplary description numerous specific details are set forth in order to provide a more thorough understanding of embodiments of the invention. It will be apparent, however, to an artisan of ordinary skill that the present invention may be practiced without incorporating all aspects of the specific details described herein. In other instances, specific features, quantities, or measurements well known to those of ordinary skill in the art have not been described in detail so as not to obscure the invention. Readers should note that although examples of the invention are set forth herein, the claims, and the full scope of any equivalents, are what define the metes and bounds of the invention.

Figure 1:
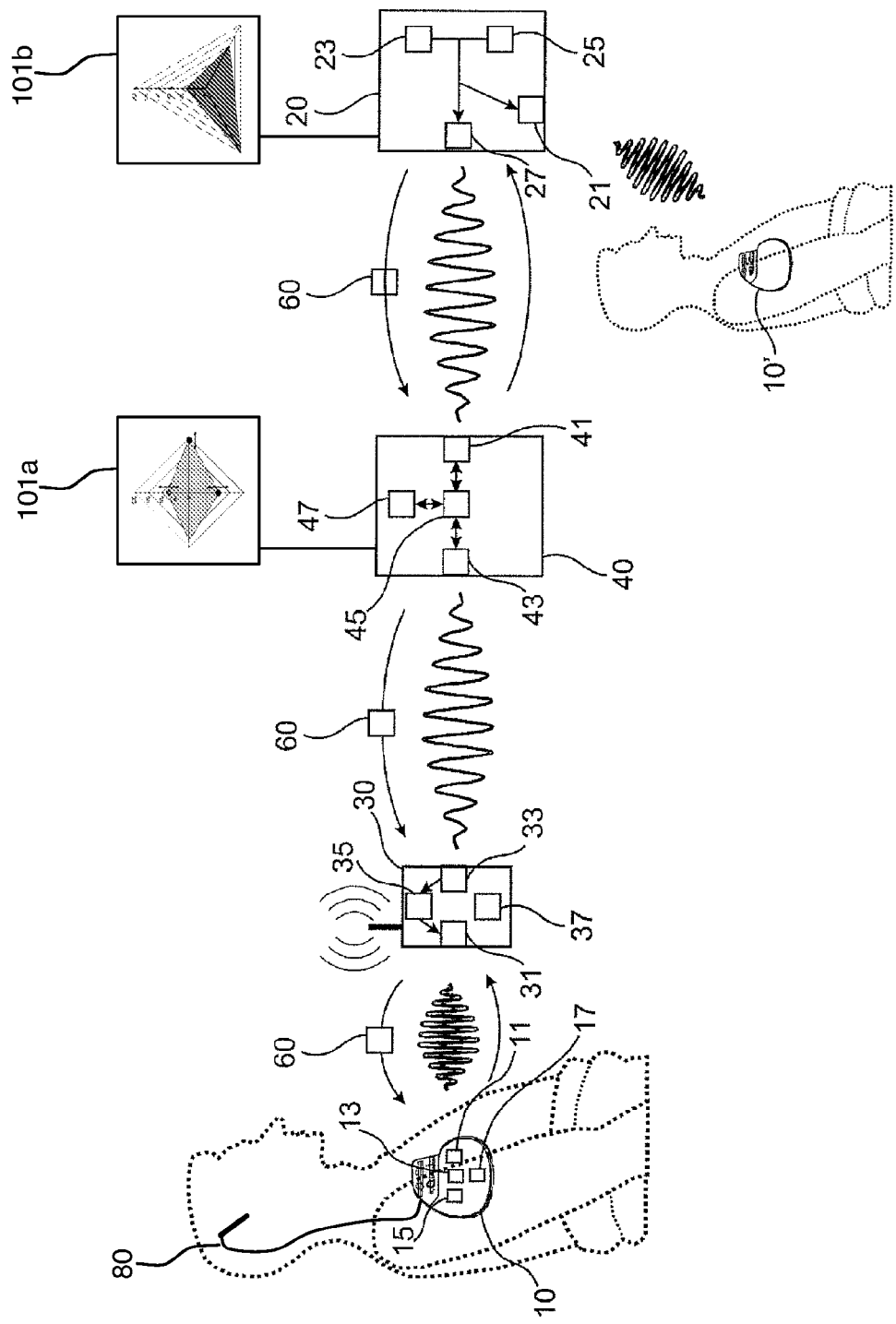
FIG. 1 illustrates an architectural view of the system.

FIG. 1 illustrates an architectural view of the system. Implant 10, which may for example represent a neurostimulator, is coupled with electrode 80 for deep brain stimulation of a patient, shown in dotted lines. Electrode 80 is positioned in the patient's brain in such a way that the target region of stimulation for treatment of Parkinson's disease is the subthalamic nucleus or for essential tremor is the ventral thalamus and/or for dystonia is the globus pallidus. The nucleus accumbens is the target region for stimulation for treatment of depression. The corresponding target region or regions in the patient's brain are stimulated either when there is an acute necessity because of a patient's health status, or continuously according to predefined signal generator settings or program parameters within implant 10. Regardless of the stimulation type, power is utilized according to the specified programming, and thus power consumption and recharge-intervals are known once the program parameters for electrical stimulation are set.

Embodiments of the invention may also be utilized with spinal cord stimulation or any other electrical stimulation type to manipulate and observe power parameters as a function of the available programming parameters of the implantable device. Embodiments of the invention show exemplary parameters such as frequency, amplitude and pulse width, however any parameters that effect power utilization may be displayed and manipulated with one or more embodiments of the invention.

Referring again to FIG. 1, implant 10' may be programmed directly via programming device 20, for example via computer display 101b. Computer display 101b is illustrated with graphics associated with power utilization according to programming parameter values for example. In this scenario, programming device 20 is brought in proximity to implant 10' for programming. Desired programming parameters are accepted by programming device 20 via an input associated with programming device 20 and/or computer display 101b, for example a touch screen, mouse, keyboard or any other type of input device.

In addition, implant 10 may be remotely programmed, for example from central service center 40, for example via patient device 30. In this scenario, patient device 30 is located in proximity to implant 10 and is used as a relay station for a data link to central service center 40. Central service center 40 is connected to computer display 101a, for example associated with a physician. Computer display 101a is illustrated with graphics associated with power utilization according to programming parameter values wherein computer display 101a may show the same or different graphics displays that are shown on computer display 101b. For example, computer display 101a may show program parameters and the calculated power usage while computer display 101b may show program parameters, power usage and calculating remaining service time. In this configuration, central service center 40 having computer display 101a and/or programming device 20 having computer display 101b each implement a clinical programmer apparatus to directly or indirectly wirelessly program an IPG.

Implant 10 may generally include a data communication interface 11 for bidirectional wireless data communication with the patient device 30, also a programmable controller 13 and a memory 15 configured to hold program parameters for example. The programmable controller 13 is connected to both the memory 15 and also the data communication interface 11. One or more embodiments of implant 10 may include a second data communication interface 17, via which the implant may be programmed with a proximally placed programming head of a programming device.

Programming device 20 generally includes a data communication interface 21 for a direct wireless data communication with the implant 10. A programming unit 23 is connected to this data communication interface 21, which is additionally connected to a memory 25 for storing programming parameters. Programming unit 23 is configured to include at least one power related programming parameter stored in the memory 25 to a particular programming instruction 60 that is communicated to an implant.

Instead of using a direct wireless data communication interface between programming device 20 and the implant in the example of implant 10' (as shown by dashed lines at the bottom right in the figure), the programming of implant 10 may also be performed remotely via the patient device 30 and central service center 40. For this purpose, patient device 30 has first data communication interface 31 that is compatible with the data communication interface 11 of implant 10. In addition, patient device 30 has second data communication interface 33, via which the patient device may establish a data link to central service center 40. The first and the second data communication interfaces 31 and 33 of the patient device 30 are connected to a patient device controller 35. In addition, the patient device 30 also has a memory 37, which is also connected to the patient device controller 35. Similarly, central service center 40 may have first data communication interface 41 for communicating with programming device 20. Programming device 20 may communicate with first data communication interface 41 via second data communication interface 27 for example. In addition, central service center 40 may include second data communication interface 43 configured for example to communicate with second data communication interface 33 of patient device 30. Central service center 40 may also be configured with control unit 45 and memory 47 connected thereto.

Figure 2:
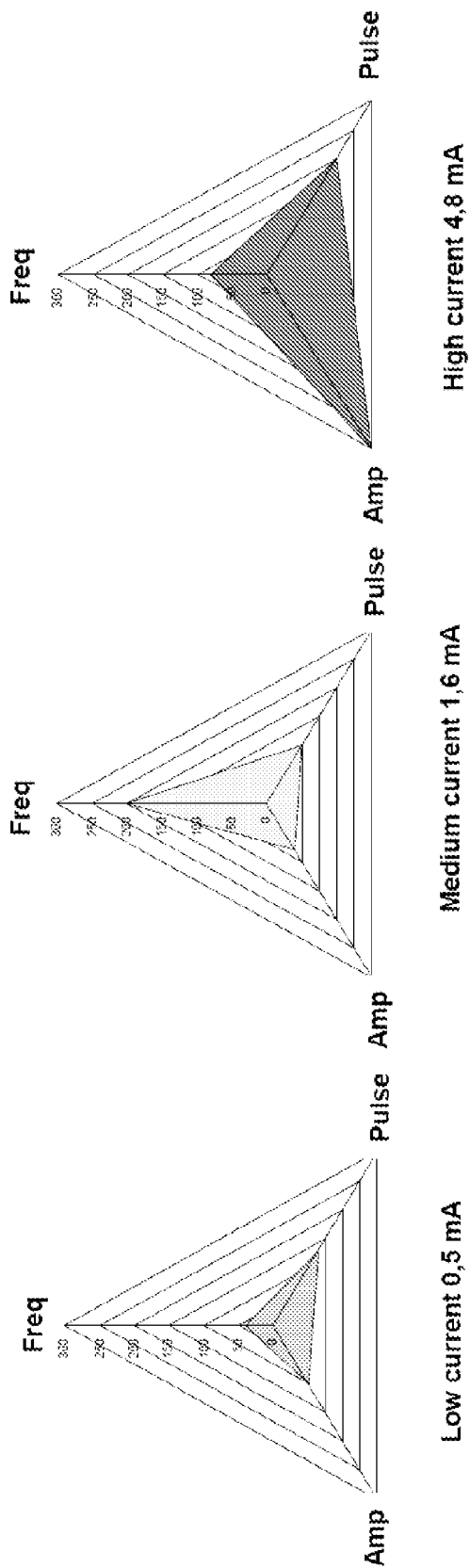
FIG. 2 illustrates an embodiment of display output for three different programming parameter triplet values.

FIG. 2 illustrates an embodiment of display output, for example as shown on computer display 101a or 101b, for three different programming parameter triplet values. Each of the three exemplary displays in the figure shows values for programming parameters on three axes related to (clockwise from top) frequency of pulse, pulse width and voltage amplitude associated with the electrical stimulation pulse. The unique display shows a surface area generally connecting the programming parameter values on each respective axis wherein the color of the surface shows colors associated with power consumption. In one or more embodiments, three colors may be utilized when displaying the surface to show low, medium and high power consumption based on the values of the programming parameters as displayed. These are shown as a low power, medium power and high power respectively from left to right wherein the current utilized, for example per a given time unit is 0.5 mA, 1.6 mA and 4.8 mA based on the various programming parameters value settings indicated on the respective axes. Alternatively, any number of axes and any number of two or more colors may be utilized in one or more embodiments of the invention, for example acceptable or non-advisable as a first color and second color respectively.

Figure 3:
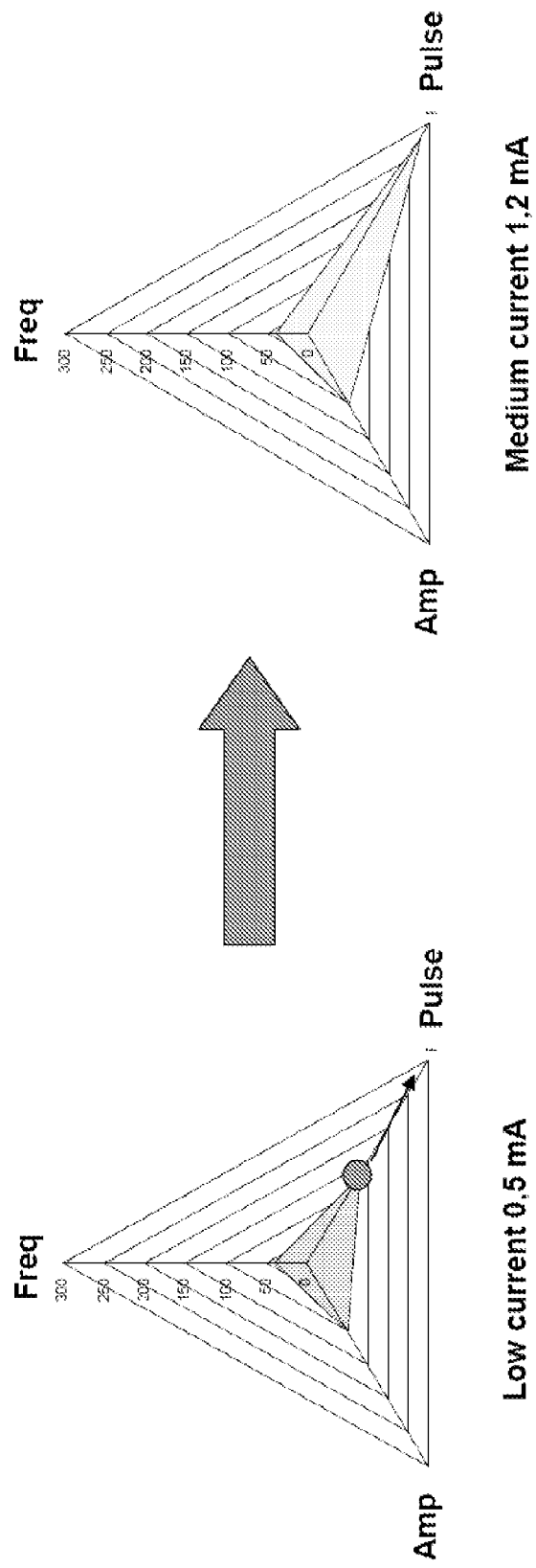
FIG. 3 illustrates an embodiment of display output that demonstrates that an increase in pulse width, given the same voltage amplitude and frequency results in different power consumption as shown.

FIG. 3 illustrates an embodiment of display output that demonstrates that an increase in pulse width, given the same voltage amplitude and frequency results in different power consumption as shown. This occurs when the apparatus accepts an increase of the pulse width on the left side of the figure that results in the pulse width on the right side of the figure. In this case, the power consumption, which corresponds to the current for a given impedance, rises from 0.5 mA to 1.2 mA. As shown, the color for example of the surface connecting the programming parameters values on each respective axis differs from the left display to the right display so long as the power consumption traverses a predefined value.

Figure 4:
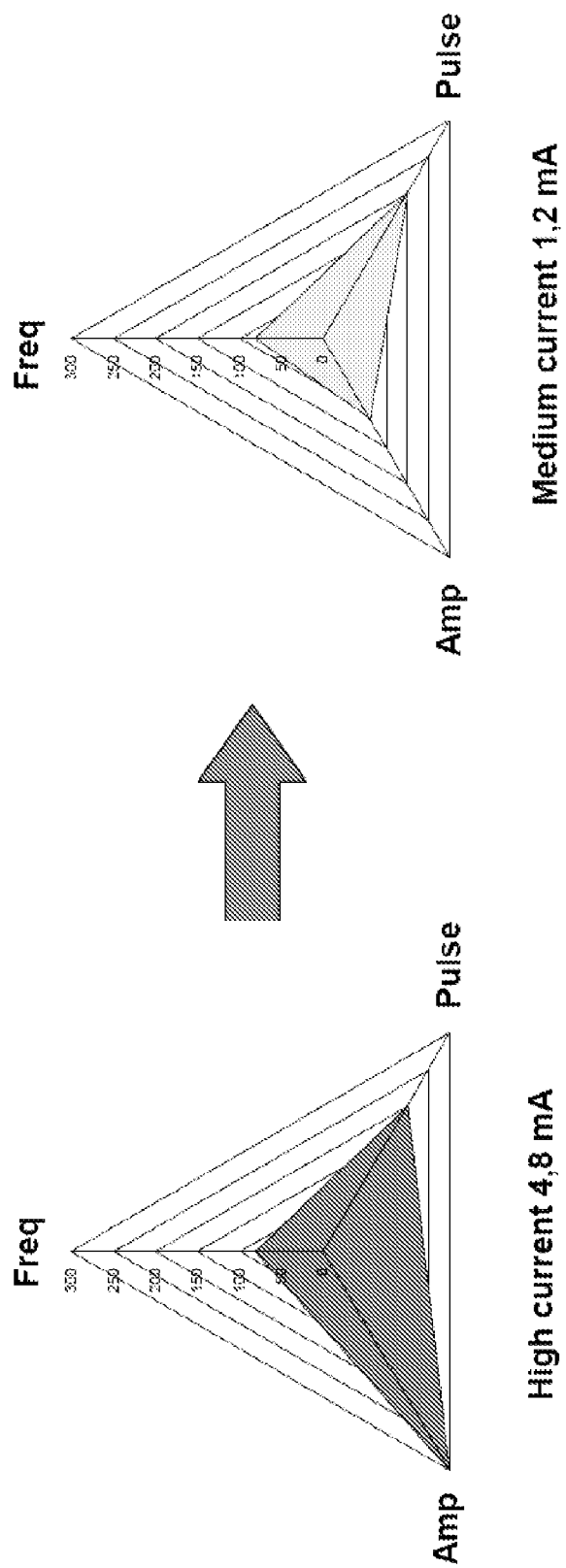
FIG. 4 illustrates an embodiment of the display output that demonstrates that a decrease in voltage amplitude, given the same pulse width and frequency results in different power consumption as shown.

FIG. 4 illustrates an embodiment of the display output that demonstrates that a decrease in voltage amplitude, given the same pulse width and frequency results in different power consumption as shown. This occurs when the apparatus accepts a decrease of the voltage amplitude on the left side of the figure that results in the voltage amplitude on the right side of the figure. In this case, the power consumption, decreases from 4.8 mA to 1.2 mA. As shown, the color for example of the surface connecting the programming parameters values on each respective axis differs from the left display to the right display so long as the power consumption traverses a predefined value.

In one or more embodiments of the invention, input is accepted by the apparatus from an input device, i.e., keyboard, mouse, touch screen, or any other device. In addition, embodiments of the invention may utilize a maximum setting so that once the maximum is set, attempts to increase any other programming parameter, i.e., increase the value away from the origin that connects the axes, is disallowed until the user inputs a lower value for a given programming parameter.

Figure 5:
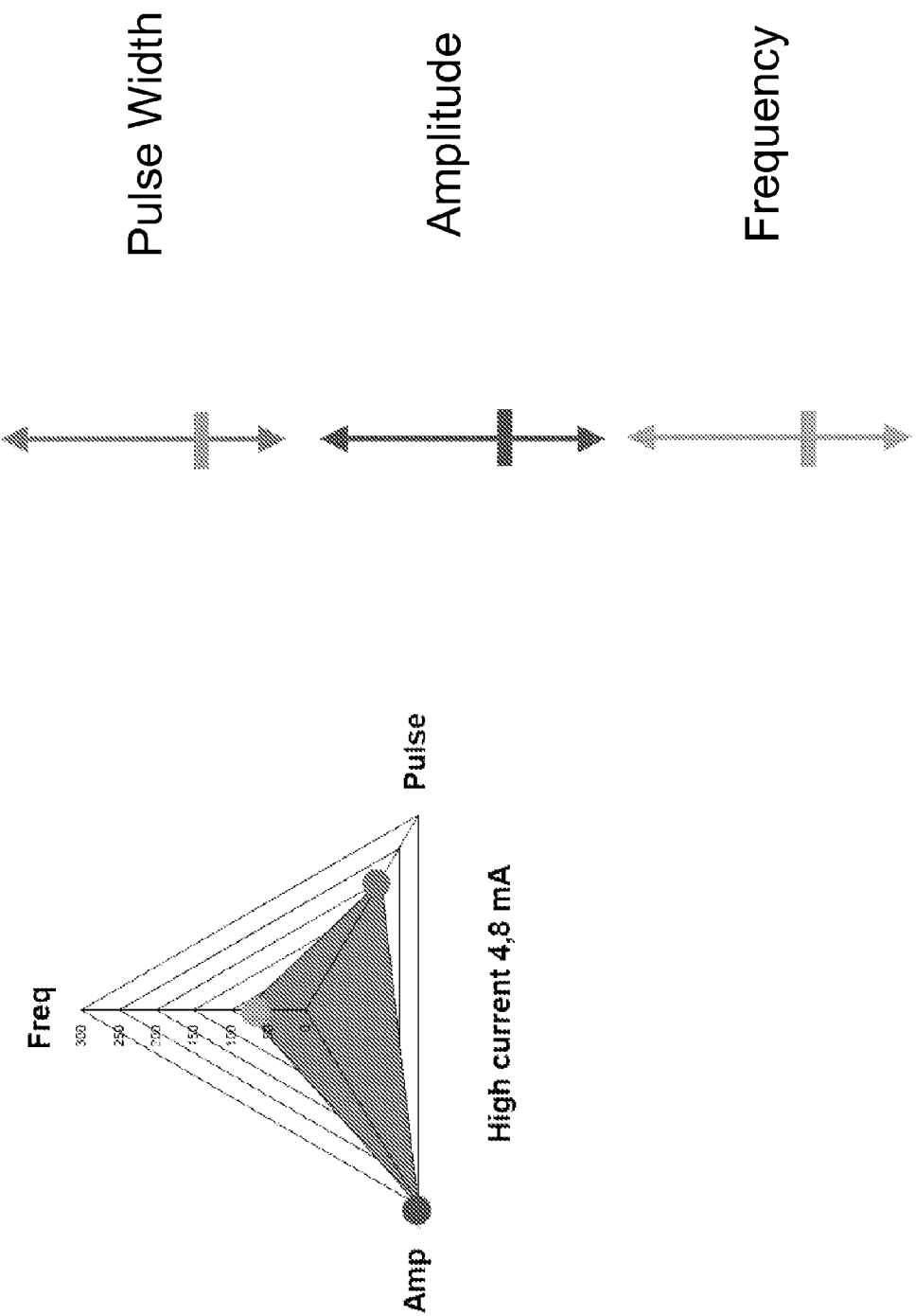
FIG. 5 illustrates an embodiment of the input interface that is driven by the input device and shown on a computer display for example.

FIG. 5 illustrates an embodiment of the input interface that is driven by the input device and shown on computer display 101a and/or 101b. In one or more embodiments of the invention, the input interface includes a circle on a respective programming parameter axis, or a respective slider interface widget (shown on the right of the figure), while the input device is a touch screen coupled with computer display 101a and/or 101b.

Figure 6:
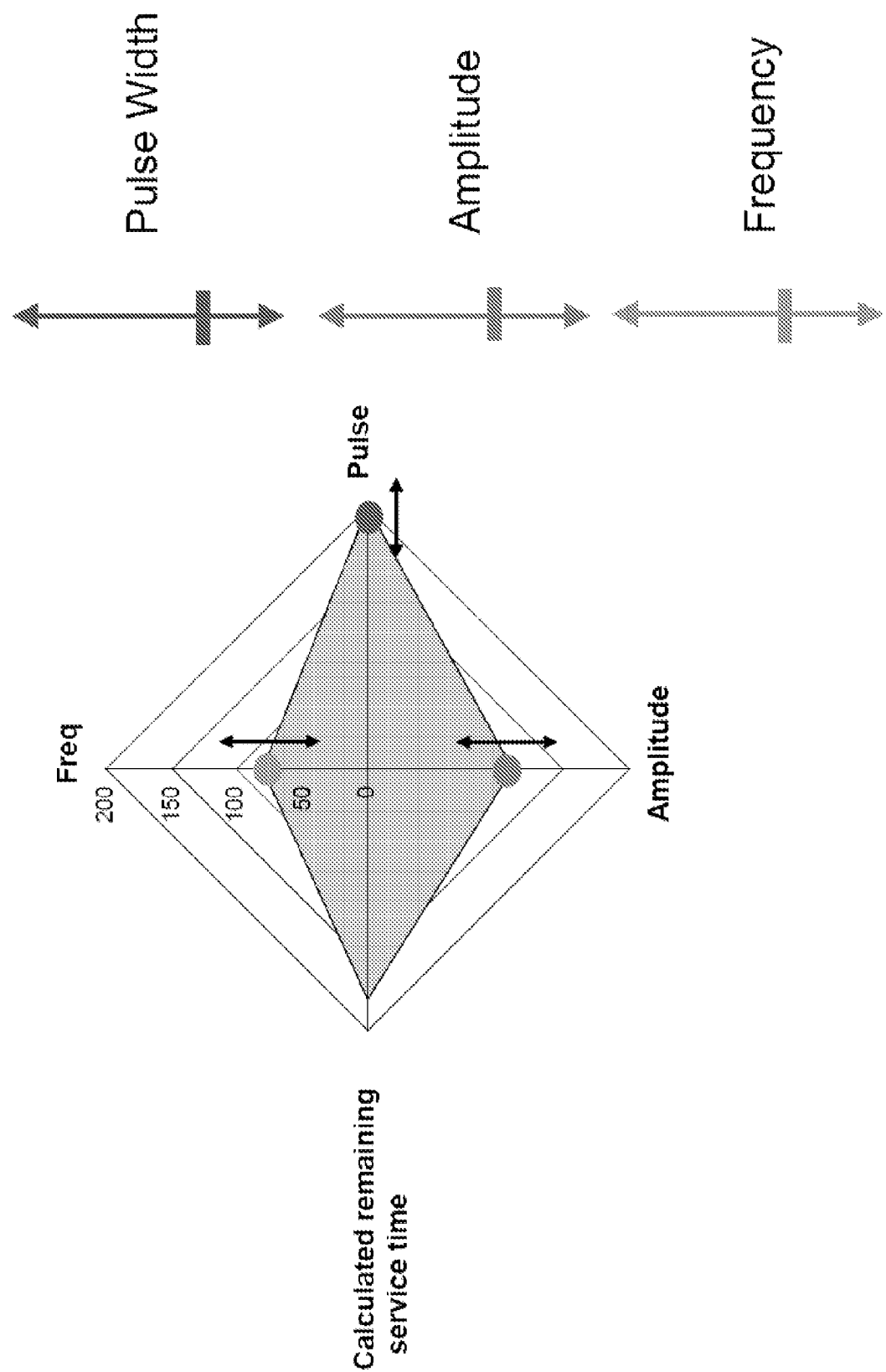
FIG. 6 illustrates an embodiment of the display output having an extra axis that is configured to display the power consumption or inversely the remaining service time based on the programming parameter values set on the other axes.

FIG. 6 illustrates an embodiment of the display output having an extra axis that is configured to display the power consumption, or inversely the remaining service time based on the programming parameter values set on the other axes. In one or more embodiments the power consumption or remaining service time may be toggled, for example by accepting a user gesture such as a double tap on a touch screen. The apparatus accepts input as per FIG. 5, i.e., accepts user gestures for example via a touch screen input device that alter the power consumption. When the power consumption as calculated by the apparatus changes, (for example as represented by the current usage of the left pointing axis), the remaining service time value may be updated in which case the surface as shown changes shape, e.g., the left side of the surface traverses to the right or left as programming parameter value inputs are accepted by the system.

Figure 7:
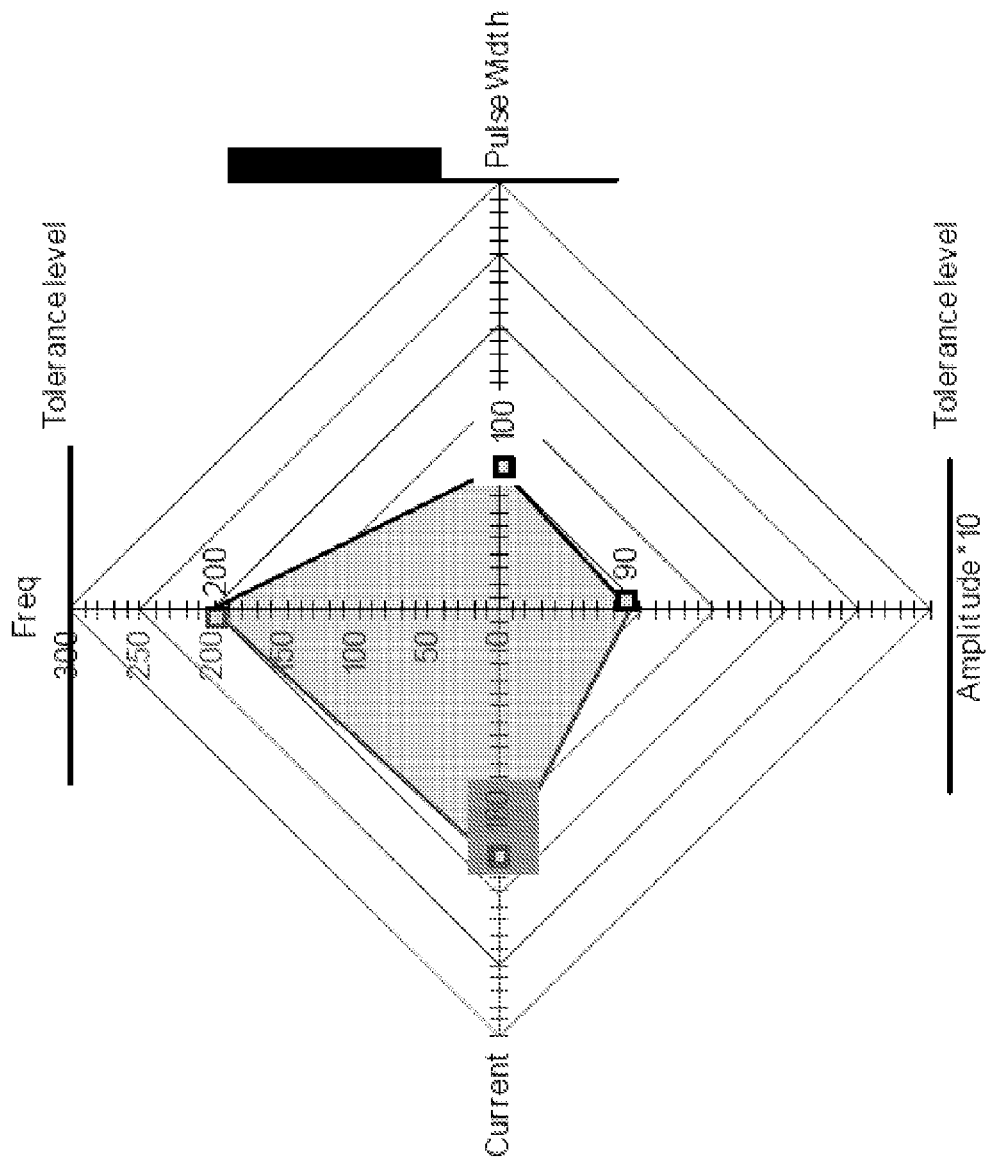
FIG. 7 illustrates tolerance level maximum values utilized in one or more embodiments of the invention and optional calculation of programming parameter values based on an input power consumption setting.

FIG. 7 illustrates tolerance level maximum values utilized in one or more embodiments of the invention and optional calculation of programming parameter values based on an input power consumption setting. The maximum values may be utilized in combination so that the horizontal and vertical lines that represent the maximum values move as one of the other programming parameter value changes. In addition, in one or more embodiments of the invention, the desired remaining service time may itself also be altered, i.e., moved left or right wherein the apparatus calculates new values that increase or decrease the programming parameter values together proportionally, in a preferential manner (pulse width first, then electrical amplitude, then frequency for example), or in any other manner that satisfies the power consumption equation for the particular settable programming parameters. In one or more embodiments of the invention, Current=K*PW*F*V where K is a constant that depends on the inverse of the impedance of the stimulation electrode and lead line, PW is the pulse width in units of time, F is the frequency of the pulses per unit time and V is the voltage amplitude. Multiplying both sides of the equation by the voltage V, results in power, i.e., V*Current. Hence if changing Current by accepting a user input to move the value for power consumption to a different value, then by solving for one of the other variables, or proportionally lowering or raising one or more variables the apparatus may automatically update the display to show calculated values for programming parameters based on the desired power consumption.

While the invention herein disclosed has been described by means of specific embodiments and applications thereof, numerous modifications and variations could be made thereto by those skilled in the art without departing from the scope of the invention set forth in the claims.

What is claimed is:

1. A clinical programmer comprising:
   a computer;
   a display coupled with said computer;
   an input device coupled with said computer;
   said computer configured to
      accept a plurality of programming parameter values via said input device;
         wherein said plurality of programming parameter values include at least voltage amplitude and frequency
         or
         pulse width and frequency;
      present said plurality of programming parameter values on said display on respective axes of a graph;

calculate a power consumption based on said plurality of programming parameter values accepted from said input device;

draw a first color between said plurality of programming parameter values if said power consumption value is below a first threshold and draw a second color between said plurality of programming parameter values if said power consumption value is above or equal to said first threshold; and, wherein said plurality of programming parameters values are configured to be changed on a respective axis associated with each programming parameter of said plurality of programming parameter values using said input device, such that said computer is further configured to automatically calculate new programming parameter values to achieve a desired energy consumption from said changed programming parameter values.

2. The clinical programmer of claim 1 wherein said computer is further configured to draw a third color between said plurality of programming parameter values if said power consumption value above or equal to a second threshold.

3. The clinical programmer of claim 1 wherein said graph comprises at least one other axis that is calculated based on said plurality of programming parameter values.

4. The clinical programmer of claim 1 wherein said computer is further configured to
- accept a desired power consumption level via said input device; and,
- set at least one of said plurality programming parameter values so that said plurality of programming values correspond to said desired power consumption level.

5. The clinical programmer of claim 1 wherein said graph comprises at least one tolerance level displayed on at least one axis of said graph.

6. The clinical programmer of claim 1 wherein said input device is a touch screen coupled with said display.

7. The clinical programmer of claim 1 wherein said input device is mouse.

8. The clinical programmer of claim 1 wherein said input device is keyboard.

9. A method for graphical display and manipulation of program parameters on a clinical programmer comprising:
- accepting a plurality of programming parameter values via an input device coupled with a computer;
  - wherein said accepting said plurality of programming parameter values include
    - at least
      - accepting voltage amplitude and frequency
      - or
      - accepting pulse width and frequency;
- presenting said plurality of programming parameter values on respective axes of a graph on a display coupled with said computer;
- calculating a power consumption based on said plurality of programming parameter values accepted from said input device;
- drawing a first color between said plurality of programming parameter values if said power consumption value is below a first threshold and drawing a second color between said plurality of programming parameter values if said power consumption value is above or equal to said first threshold; and
- changing said plurality of programming parameters values on a respective axis associated with each programming parameter of said plurality of programming parameter values using said input device, and automatically calculating new programming parameter values to achieve a desired energy consumption from said changed programming parameter values using said computer.

10. The method of claim 9 further comprising drawing a third color between said plurality of programming parameter values if said power consumption value above or equal to a second threshold.

11. The method of claim 9 wherein said graph comprises at least one other axis that is calculated based on said plurality of programming parameter values.

12. The method of claim 9 wherein said computer is further configured to
- accepting a desired power consumption level via said input device; and,
- setting at least one of said plurality programming parameter values so that said plurality of programming values correspond to said desired power consumption level.

13. The method of claim 9 further comprising displaying at least one tolerance level on at least one axis of said graph.

14. The method of claim 9 wherein said accepting comprises accepting via an input device comprising a touch screen coupled with said display.

15. The method of claim 9 wherein said accepting comprises accepting via an input device comprising a mouse.

16. The method of claim 9 wherein said accepting comprises accepting via an input device comprising a keyboard.

* * * * *